United States Patent [19]

Hies et al.

[11] Patent Number: 5,147,548
[45] Date of Patent: Sep. 15, 1992

[54] COLOSTRUM FILTERED STERILE

[75] Inventors: Henry Hies, Rodermark; Wolfgang Moller, Oberursel; Herbert Dichtelmuller, Sulzbach; Wolfgang Stephan, Dreieich, all of Fed. Rep. of Germany

[73] Assignee: Biotest Pharma GmbH, Dreieich, Fed. Rep. of Germany

[21] Appl. No.: 745,036

[22] Filed: Aug. 14, 1991

[30] Foreign Application Priority Data

Aug. 21, 1990 [DE] Fed. Rep. of Germany ....... 4026365

[51] Int. Cl.$^5$ ............................................. B01D 6/16
[52] U.S. Cl. ..................................... 210/639; 210/651
[58] Field of Search ............... 210/639, 641, 652, 650; 426/74; 530/361

[56] References Cited

U.S. PATENT DOCUMENTS

| | | | |
|---|---|---|---|
| 3,911,108 | 10/1975 | Singh | 424/86 |
| 4,051,235 | 9/1977 | Plymate | 424/85 |
| 4,140,806 | 2/1979 | Glimenius et al. | 426/491 |
| 4,784,850 | 11/1988 | Abraham | 424/87 |
| 4,834,974 | 3/1989 | Stott et al. | 530/387 X |

FOREIGN PATENT DOCUMENTS

| | | |
|---|---|---|
| 0052862 | 6/1982 | European Pat. Off. |
| 0102831 | 3/1984 | European Pat. Off. |
| 0173999 | 3/1986 | European Pat. Off. |
| 0334776 | 9/1989 | European Pat. Off. |
| 0363896 | 4/1990 | European Pat. Off. |
| 3432718 | 5/1986 | Fed. Rep. of Germany |
| 2813984 | 11/1987 | Fed. Rep. of Germany |
| 3743440 | 6/1989 | Fed. Rep. of Germany |
| 8601687 | 3/1986 | Int'l Pat. Institute |

OTHER PUBLICATIONS

Deutsche Molkereizeitung, 1989, pp. 1602–1608, particularly p. 1603, right col., first paragraph. "Die Anwendung der Mikrofiltration", Damerow et al.

Article, B. Reckter, "Milchsubstanzen gegen Montezumas Rache", Physis [Jan. 2989], 32.

Primary Examiner—Frank Spear
Attorney, Agent, or Firm—Sprung Horn Kramer & Woods

[57] ABSTRACT

A sterile-filtered colostrum solution that contains casein is made by adjusting the pH of a colostrum solution to 2.5 to 3.5 and then filtering it clear and sterile. It is preferably first defatted, and adjusted to pH 5.5 to 8 after the acid treatment but before being filtered.

16 Claims, No Drawings

COLOSTRUM FILTERED STERILE

BACKGROUND OF THE INVENTION

The invention relates to a special colostrum and a method of manufacturing it.

Bovine colostrum collected within 30 hours of calving contains high levels of immunoglobulins G, A, and M. The substance also contains other proteins that make it ideal for providing calves with a passive immunity, especially against enteropathogenic germs, during their first few days. This property of the colostrum has led to the development of several methods of isolating the immunoglobulins for use against gastro-intestinal disorders in humans in particular.

German C 2,813,984 and C 3,432,718, European B 102,831, and U.S. Pat. Nos. 4,051,235, 4,784,850, and 4,834,974 for example describe the manufacture from colostrum of preparations that contain immunoglobulins. These preparations also contain some other proteins. What is common to all, however, is that they are made from colostral serum (whey) once the casein has been acid or enzyme precipitated and separated. The casein must always be eliminated when the colostrum is to be either filtered sterile or ultrafiltered.

Bovine colostrum is about 12% protein and contains cell particles and a large number of bacteria.

There are between $10^6$ and $10^8$ germs/ml in raw colostrum as against between $10^3$ and $10^4$ germs/ml in regular cow's milk, Pasteurization for 15 to 40 seconds at 71° to 74° C. or for 1 to 4 seconds at 85° to 90° C. for example reduces the count of pathogenic germs by 1 to 2 powers of ten, which still represents a high level of bacteria. These germs can multiply while the substance is in storage and cause severe side effects especially when it is employed to treat gastro-intestinal disorders.

U.S. Pat. No. 3,911,108 describes sterilizing colostrum and its derivatives with β-propiolactone. Another approach for example is to treat the colostrum with gamma radiation. Both methods, however, tend to denature the proteins to some extent.

Filtration sterilization, the simplest and most effective method of eliminating the bacteria and the method that best protects the proteins, cannot be employed with colostrum because the casein immediately clogs up the filter. All methods that are intended to produce a preparation that can be filtered sterile or ultrafiltered accordingly start from the optionally defatted whey. The casein is acid or enzyme precipitated and centrifuged out while the whey is being prepared. The whey or its isolated fractions can then be ultrafiltered and filtered sterile.

German C 2,813,984 expressly asserts that skimming and clarification (casein precipitation) must be very extensive to prevent clogging the filter and ultrafilter later.

Eliminating the casein by precipitation, however, has serious drawbacks with respect to using or purifying the colostrum later.

1. As much as 40% of the immunoglobulins can be trapped along with the casein in the precipitate and coprecipitate and lost.

2. Centrifuging out the precipitate is complicated and expensive, especially considering the yield of immunoglobulins.

3. Casein itself has beneficial therapeutic properties that in particular augment the actions of the immunoglobulins in gastro-intestinal disorders. Opiate-like substances are released from the casein and help suppress peristalsis and promote the resorption of electrolytes and water. These activities have also been ascribed to the intact casein (B. Recker, Physis [January 1989], 32).

It is generally desirable to alter the protein composition of the colostrum as little as possible because it is already ideal for the prevention and treatment of gastrointestinal infections and disorders. In addition to the immunoglobulins and casein for instance, such proteins as lysozyme, lactoferrin, and the peroxidases carry out significant functions in the defense against bacterial infections. A majority of these important proteins, however, are either separated out or inactivated by casein precipitation and pasteurization.

The object of the present invention is accordingly a method of removing bacteria from colostrum by filter sterilization that will retain as many of the protein constituents of the original colostrum as possible.

It has surprisingly been discovered that colostrum can, without previously removing the casein, be filtered clear and sterile by adjusting it, optionally defatted, to a pH less than 3.5. Although the casein precipitates at a pH of 5 to 4, it will return to solution as the pH continues to drop. The acidic solution differs so extensively from the original colostrum that it can be filtered sterile.

The colostrum so acidified can be restored to its original pH before being filtered. As the acidity is neutralized, the casein will precipitate again at a pH of 4 to 5 and return to solution at approximately 5.5. The resulting colostrum is surprisingly even somewhat easier to filter than the defatted acidic colostrum at a pH of less than 3.5.

When decreasing the pH it is important to allow the casein to remain precipitated only briefly and to continue lowering the pH until the casein returns to solution. Preferably, the colostrum is substantially continuously acidified. If the casein remains precipitated too long and is returned too late to solution, the colostrum will be definitely more difficult to filter.

In one preferred embodiment of the invention the colostrum is defatted by measures that are in themselves known and diluted with a sodium chloride solution to 20 grams of protein per liter. Hydrochloric acid is added rapidly to adjust the pH of the colostrum to 2.0 to 3.5 and preferably 2.8 to 3.2, until the precipitate that accompanies the acidification returns to solution. The temperature should not increase beyond 45° C. during the acidification to prevent denaturing the immunoglobulins.

The colostrum's pH can optionally be restored to its original value immediately or later by adding sodium hydroxide solution. As the pH increases, the casein will temporarily precipitate again and immediately return to solution.

Once the defatted colostrum has been subjected to the foregoing treatment, it can easily be filtered sterile or ultrafiltered by known methods. It can be filtered clear through a depth filter for example. The colostrum so clarified can then be filtered sterile through either a membrane or a depth filter. The defatted colostrum can also be ultrafiltered or dialyzed before or after being filtered sterile.

The material can be filtered even more easily if such filter aids as Hyflo Supercell for example are added.

The filtered-sterile defatted colostrum is preferably adjusted to 20 to 70 grams of protein per liter, although it can also be concentrated to 120 g/l. The concentration of lactose can also be decreased by dialysis and the ionic environment adjusted to make the resulting preparation especially appropriate for treating gastrointestinal disorders. The filtered-sterile defatted colostrum can also be freeze-dried or fractionated into its protein constituents.

Although the filtration is preferably carried out with defatted colostrum, the method in accordance with the invention is also appropriate for colostrum that has not been defatted. The rate of filtration is admittedly definitely lower than that of defatted colostrum but still substantially above that of colostrum that has not been acid treated.

The invention will now be illustrated with reference to the following examples.

EXAMPLE 1

500 ml of frozen colostrum were treated with 500 ml of water and thawed to 37° C. The lipid fraction was separated by centrifugation and the resulting defatted colostrum diluted with 2000 ml of a 100 mM sodium chloride solution.

The pH was adjusted to 3.0 in 30 seconds with 1N hydrochloric acid. One hour later the solution (approximately 3 l) was pumped through a depth filter (Seitz Supra 80) with an area of 150 cm$^2$ at a pressure of 0.5 bar to clarify it. The clarification was followed by sterilization by filtration through a stack of membranes with pores measuring 5, 1.2, 0.65, and 0.22$\mu$.

For comparison, the colostrum was similarly defatted and diluted but without being acidified to pH 3.0. It was possible to filter only 150 ml of this defatted material through the depth filter, even at a pressure as high as 3 bar. It was impossible to filter sterile through membranes.

EXAMPLE 2

500 ml of colostrum were acidified to pH 3.0 as in Example 1. Two hours later the pH was adjusted to 6.5 and the material filtered clear and sterile as in Example 1. It was now possible to filter the material through a depth filter at a pressure of 0.2 bar.

EXAMPLE 3

500 ml of colostrum were treated as in Example 2 and filtered. 3 g of a filter aid (Hyflo Supercell) were added to every 100 ml of the dilute defatted colostrum before it was filtered through Supra 80. The addition improved the rate of depth filtration. The process was followed by sterilization by filtration as in Example 1.

A reference batch of defatted colostrum that had not been acidified to 3.0 as in Example 1 was prepared. Once the filter aid was added, it was possible to filter the material through the Supra 80 at a pressure of 1 bar, but filtration sterilization through a membrane was impossible.

EXAMPLE 4

500 ml of colostrum was defatted as in Example 1 and then adjusted undiluted to a pH of 2.8. The pH was then raised back to 6.5. The colostrum was, once 3% filter aid had been added, filtered clear through Supra 80 and then sterile through a Seitz EK 1 filter.

EXAMPLE 5

500 ml of colostrum were diluted with 2500 ml of an 80 mM sodium chloride solution and the pH adjusted to 3.1 with 1N hydrochloric acid. The pH was then increased to 7.0 and the fatty colostrum, to which 3% of a filter aid (Hyflo Supercell) had been added, was then filtered clear through Supra 80 and sterile through an EK 1 filter.

Although the rate of both clarification and sterilization filtration was lower than that of the defatted colostrum, it was possible to filter the material through an accordingly larger area. It was, however, impossible to filter this colostrum, which had been neither acidified nor defatted, even through the Supra 80 cartridge subject to the same conditions.

EXAMPLE 6

1 liter of filtered-sterile defatted colostrum from Example 3 was dialyzed over a 0.9 m$^2$ 10 000 D membrane against 5 times as much of an 80 mM sodium chloride solution and then ultrafiltered through the same membrane.

A similarly diluted but not acidified defatted colostrum was subjected to the same dialysis and ultrafiltration for comparison.

In this particular test, the rate of permeate flow of the colostrum treated in accordance with the invention was 11 l per hour per square meter of membrane at a transmembrane pressure of 1.2 bar. Ultrafiltration concentrated the colostrum to 110 g of protein per liter.

The transmembrane pressure applied to the reference substance rapidly increased during the dialysis to more than 2 bar, and the flow rate decreased rapidly. The membrane became obstructed and the dialysis had to be discontinued. No ultrafiltration was possible at all.

It will be appreciated that the instant specification and claims are set forth by way of illustration and not limitation, and that various modifications and changes may be made without departing from the spirit and scope of the present invention.

What is claimed is:

1. Sterile filtered colostrum containing sterile casein.
2. Colostrum according to claim 1, having substantially its natural casein content.
3. Colostrum according to claim 1, of bovine origin.
4. Defatted colostrum according to claim 1.
5. Colostrum according to claim 1, containing about 1 to 120 grams of protein per liter.
6. Colostrum according to claim 5, containing about 1 to 50 grams of protein per liter.
7. Colostrum according to claim 1, containing less than about 100 mg of lactose per liter.
8. A method of obtaining a sterile-filtered colostrum that contains casein, comprising:
   a) acidifying a colostrum solution until the casein precipitates and then returns to solution and
   b) sterile filtering the resulting solution.
9. The method according to claim 8, wherein the colostrum solution is diluted prior to acidification.
10. The method according to claim 8, wherein the pH of the colostrum solution is acidified to about 2.5 to 3.5.
11. The method according to claim 8, wherein between steps (a) and (b) the pH is brought back to about 5.5 to 8.
12. The method according to claim 8, wherein the colostrum solution is produced in step (a) is filtered clear before being sterile-filtered.
13. The method according to claim 8, wherein in step (b) there is employed a filter aid.
14. The method according to claim 8, wherein the colostrum is defatted prior to step (a).
15. The method according to claim 12, wherein the sterile filtration is effected through either a depth filter or a membrane.
16. The product produced by the process of claim 8.

* * * * *